United States Patent [19]

Barberet et al.

[11] Patent Number: Plant 5,445

[45] Date of Patent: Apr. 23, 1985

[54] CARNATION NAMED LONDELIEN

[75] Inventors: Nicole Barberet; Yves Ducloux, both of Antibes, France

[73] Assignee: Laboratoire de Physiologie Vegetale de La Londe, Antibes, France

[21] Appl. No.: 516,564

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation cultivar particularly distinguished by the Brick Red and Magenta Rose coloration of its relatively small blossoms which are borne on straight, rather rigid peduncles branching from a strong, rather rigid, upright stem having somewhat abundant foliage and a vigorous, upright growth habit which is rather resistant to *Fusarium oxysporum.*

1 Drawing Figure

BACKGROUND OF THE NEW PLANT

Our new spray carnation is the result of breeding efforts carried on by us at La Londe, Les Maures, France, since 1977 with the object of developing new carnation varieties having nice color and good quality of plant growth and resistance to *Fusarium oxysporum.* This new plant originated as a seedling produced by our crossing of selected and individually identified plants growing among our stock of spray carnations maintained at La Londe for breeding purposes and this particular seedling was selected by us for propagation and test because of its very distinctive flowers having generally Brick Red colored petals with Magenta Rose streaks and petal margins, its apparently favorable growth habit and its *Fusarium oxysporum resistance. This discovery plant was reproduced by us at La Londe, by means of cuttings, and the result of that propagation appearing favorable with respect to retention of the novel characteristics of the parent plant, we continued such propagation through several successive generations and over a period of years thereby determining that the novel and distinctive characteristics of the discovery plant are fully retained from generation to generation and appear to be firmly fixed.*

DESCRIPTION OF THE DRAWING

Our new carnation plant is illustrated by the accompanying photographic drawing which shows, in full color, the spray of a typical flowering stem with buds and flowers in various stages of opening, the colors shown as nearly true to those specified herein as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling

Parentage:

*Seed parent.*—Stock Plant No. 73 MOR 1.

*Pollen parent.*—Stock Plant No. 9 M G 7. These unnamed carnation varieties are individually identified in our permanent records and are maintained in our carnation collection for breeding purposes at La Londe, France.

Classification:

*Botanic.*—*Dianthus caryophyllus.*

*Commercial.*—Spray carnation.

Form: Tall, erect bush with at least four stems emitted near the ground.

Height: Averaging about 107 cm. at eight months.

Main stem:

*Length.*—Less than 15 cm. due to pinching.

Branching character: Well branched from all stems.

Growth habit: Vigorous, upright and rather rigid.

Foliage:

*Quantity:* Rather abundant.

*Number of Leaves.*—At least 120.

*Leaf size.*—About 12 cm. long and 9 mm. wide, in average at the seventh node.

*Leaf shape.*—Linear with lightly curved margins.

*Texture.*—Leathery

*Color.*—Upper side — 191A. Under side — 191A.

*Ribs and Veins.*—Hardly noticeable.

*Rachis.*—Hardly noticeable.

THE BUD

Size: Medium.

*Diameter.*—About 1.3 cm. in average.

*Length.*—About 3 cm. in average.

Rate of opening: Normal for carnations.

Color of petals:

*When sepals first divide.*—Orient Pink.

*When petals begin to unfurl.*—Like at full bloom.

Sepals:

*Number.*—Five (exceptionally six).

*Shape.*—Joined at lower part with the upper part of acute form and sharply pointed at the apex. The sepals are hooded over the bud and stand up when the flower opens.

*Color.*—Inside — Greenish white. Outside — 137D and 144C.

*Striae.*—Longitudinal.

Calyx:

Shape.—Cylindrical and slightly widened at the flower.

*Splitting.*—The calyx does not split.
*Aspect.*—Smooth.
Flower stem:
*Length.*—About 72 cm.
*Character.*—Erect and rather thin.
*Color.*—189B

THE FLOWER

Blooming habit: Recurrent, blooming profusely during the midseason of Spring and Fall.
Size of bloom: Small.
*Diameter.*—About 5.3 cm. in average.
*Length.*—About 4.7 cm. in average.
Borne: In cluster.
Shape:
*When bloom first opens.*—High centered.
*When bloom matures.*—Dome-shaped.
Petalage:
*Number of petals.*—About 41 in average.
*Arrangement.*—Imbricated.
*Form.*—Fan-shaped with finely serrated outer edges.
*Texture.*—Soft.
*Appearance.*—Satiny.
*Color.*—Outer petal: Body — 35D and 64B. Base — Greenish white. Reverse side — 36A, 36D and 64B. Inside Petal: Body — 35D and 64B. Base — Greenish white. Reverse side — 36A and 36D.
Petaloids:
*Number.*—From 1 to 12.
*Size.*—Smaller than petals.
*Color.*—Same as petals.

Flower stem:
*Length.*—About 72 cm.
*Character.*—Upright and of good strength.
*Color.*—189B.
Fragrance: Absent or light.
Persistence: The petals hang on and dry.
Lasting quality: As cut flower — At least ten days in vase keeping.
Disease resistance: Rather resistant to *Fusarium oxysporum* as observed INRA, Antibes, Alpes-Maritimes, France.

REPRODUCTIVE ORGANS

Stamens:
*Number.*—From 1 to 13.
*Arrangement.*—Around the pistils.
*Anthers.*—Size: Less than 4 mm. Color: White.
*Filaments.*—Color — White.
Pistils:
*Number.*—2 Or 3.
*Styles.*—Color — White.
*Stigmas.*—Color — Lightly violet.
Character of ovaries: The ovary is lightly ribbed.

We claim:

1. A new and distinct spray carnation variety, substantially as herein shown and described, characterized by the very strong Brick Red and Magenta Rose coloring of its small blooms which are produced profusely on tall, straight and strong flowering stems, and by its vigorous and upright growth habit, abundant foliage and resistance to *Fusarium oxysporum.*

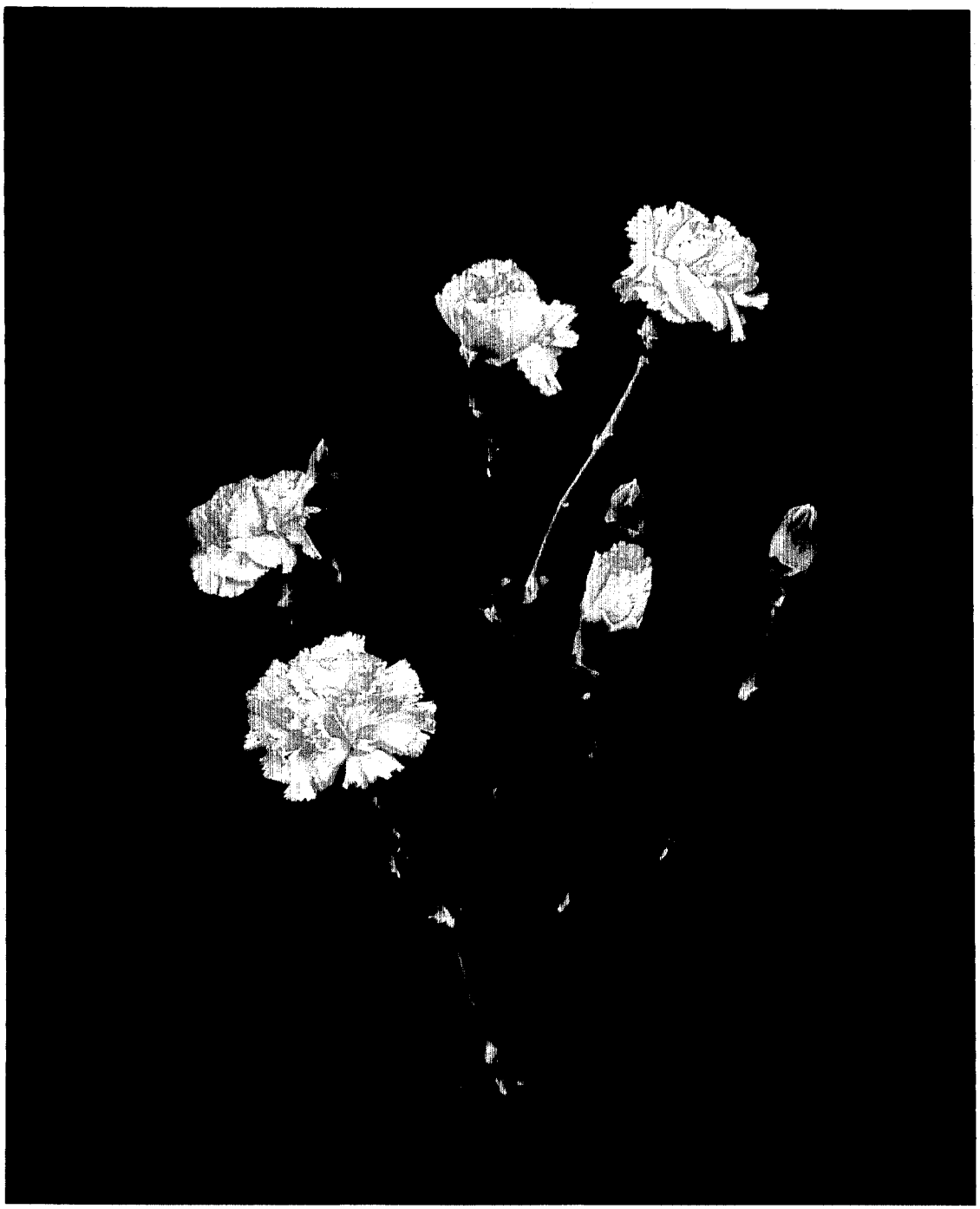

* * * * *